US011419541B2

(12) United States Patent
Bowman et al.

(10) Patent No.: US 11,419,541 B2
(45) Date of Patent: Aug. 23, 2022

(54) SYSTEMS AND METHODS FOR PATIENT SPECIFIC MODELING OF THE MECHANICAL PROPERTIES OF BONE

(71) Applicant: Ohio University, Athens, OH (US)

(72) Inventors: Lyn Bowman, Athens, OH (US); John R. Cotton, Athens, OH (US)

(73) Assignee: Ohio University, Athens, OH (US)

( * ) Notice: Subject to any disclaimer, the term of this patent is extended or adjusted under 35 U.S.C. 154(b) by 471 days.

(21) Appl. No.: 16/617,236

(22) PCT Filed: May 10, 2018

(86) PCT No.: PCT/US2018/031981
§ 371 (c)(1),
(2) Date: Nov. 26, 2019

(87) PCT Pub. No.: WO2018/222363
PCT Pub. Date: Dec. 6, 2018

(65) Prior Publication Data
US 2020/0146616 A1  May 14, 2020

Related U.S. Application Data

(60) Provisional application No. 62/512,870, filed on May 31, 2017.

(51) Int. Cl.
*A61B 5/00* (2006.01)
*A61B 5/055* (2006.01)
*G06F 9/455* (2018.01)

(52) U.S. Cl.
CPC ............ *A61B 5/4504* (2013.01); *A61B 5/055* (2013.01); *G06F 9/455* (2013.01)

(58) Field of Classification Search
CPC .............................. A61B 5/4504; A61B 5/055
See application file for complete search history.

(56) References Cited

U.S. PATENT DOCUMENTS 5,006,984 A   4/1991 Steele
5,487,395 A   1/1996 Strowe
(Continued)

FOREIGN PATENT DOCUMENTS

KR   1010952635 B1   4/2010
WO   2012089221 A1   7/2012
WO   20140169217 A2   10/2014

OTHER PUBLICATIONS

Silvio Lorenzetti et al., "A new device and method for measuring the elastic modulus of single trabeculae", Medical Engineering & Physics, vol. 33, No. 8, pp. 993-100, Mar. 31, 2011.
(Continued)

*Primary Examiner* — Joseph M Santos Rodriguez
(74) *Attorney, Agent, or Firm* — Dinsmore & Shohl LLP

(57) ABSTRACT

Methods of patient-specific modeling of the mechanical properties of bone and related systems. The methods include obtaining a bending stiffness (K) of a bone specimen non-invasively and non-destructively in a dynamic 3-point bending test, creating a mathematical mechanical model of the bone specimen, assigning an elastic modulus (E) to the bone specimen of the mathematical mechanical model, determining the flexural rigidity of the bone specimen from simulating the mathematical mechanical model, determining a discrepancy between the flexural rigidity of the bone specimen from the simulated mechanical model and based on the obtained K, adjusting the elastic modulus of the simulated mechanical model to minimize the discrepancy, adjusting the elastic modulus until an optimized elastic modulus is determined where the discrepancy is reduced below a predetermined threshold, and applying the optimized elastic modulus to the simulated mechanical model to determine a strength of the bone.

15 Claims, 1 Drawing Sheet

(56) References Cited

U.S. PATENT DOCUMENTS

| | | | |
|---|---|---|---|
| 7,485,100 | B2 | 2/2009 | Garcia-Webb et al. |
| 9,245,069 | B2 | 1/2016 | Keyak |
| 2002/0082779 | A1 | 6/2002 | Ascenzi |
| 2006/0224088 | A1 | 10/2006 | Roche |
| 2008/0208550 | A1 | 8/2008 | Ascenzi |
| 2010/0069455 | A1 | 3/2010 | Takato et al. |
| 2011/0270313 | A1 | 11/2011 | Justis et al. |
| 2013/0204164 | A1 | 8/2013 | Hansma et al. |
| 2016/0058365 | A1 | 3/2016 | Bowman et al. |

OTHER PUBLICATIONS

Daniel E. Martin, et al.—Determination of mechanical stiffness of bone by pQCT Measurements: correlation with non-destructive Mechanical four-point bending test data, Journal of Biomechanics, vol. 37, No. Aug. 8, 2004, pp. 1289-1293.

Database Medline [Online] US National Library of Medicine (NLM), Bethesda, MD, US; Aug. 2004.

Bowman Lyn et al: "A new noninvasive mechanical bending test accurately predicts ulna bending strength in cadaveric human arms", Bone, vol. 120, Nov. 26, 2018 (Nov. 26, 2018), pp. 336-346, P085589291.

Extended European Search Report pertaining to EP Application No. 18809530.1.

Communication pursuant to Rules 70(2) and 70a(2) EPC, pertaining to EP Application No. 18809530.1, dated Dec. 8, 2020.

Altenburger et al., "Mathematical Modeling of Skin-Bone Systems in Mechanical Response Tissue Analysis", Ohio University Student Expo 2011, May 13, 2011.

Charlton et al., "Accuracy of Mechanical Response Tissue Analysis (MRTA) Measurements on an Artificial Human Ulna", Ohio University Student Expo 2011, May 13, 2011.

Cotton, Jr. et al., "Ulna Simulation Assesses sensitivity to bone elastic modulus variations in a MRTA test", Abstract presented at 2012 American Society of Biomechanics 36 Annual Meeting from Aug. 15, 2012-Aug. 18, 2012, Abstract saved online at http://www.asbweb.org/conferences/2012/topics/index.html between Oct. 5, 2012-Nov. 5, 2012; pp. 231-232.

Kontulainen et al., "Strength indices from pQCT imaging predict up to 85% of variance in bone failure properties at tibial epiphysis and diaphysis", J. Musculoskelet Neuronal Interact, vol. 8, No. 4, pp. 401-409, Oct. 2008.

Magland et al., "Computationally-Optimized Bone Mechanical Modeling from High-Resolution Structural Images", PLoS ONE, vol. 7, Issue 4, Apr. 25, 2012.

"MIT and Ohio University Use Vibration in Research", The Modal Shop, Inc. News and Events, Jan. 9, 2013, www.modalshop.com/news.asp?P=MIT_And_Ohio_University_Uswe_Vibration_in_Research&NID=137.

Van Horne et al., "Precision of Mechanical Response Tissue Analysis (MRTA) Measurements", Ohio University Student Expo 2011, May 13, 2011.

Xu et al., "Flexural Rigidity and Shear Stiffness of Flagella Estimated from Induced Bends and Counterbends", Biophysical Journal 111, pp. 2759-2768, Jun. 22, 2016.

Search and Written Opinion pertaining to Application No. PCT/US2014/033816 dated Nov. 13, 2014.

International Preliminary Report on Patentability pertaining to Application No. PCT/US2014/033816 dated Oct. 13, 2015.

Search and Written Opinion pertaining to Application No. PCT/US2018/031981 dated Aug. 8, 2018.

Search and Written Opinion pertaining to Application No. PCT/US2019/014662 dated Apr. 11, 2019.

Office Action pertaining to Application No. EP14783154.9 dated Nov. 27, 2015.

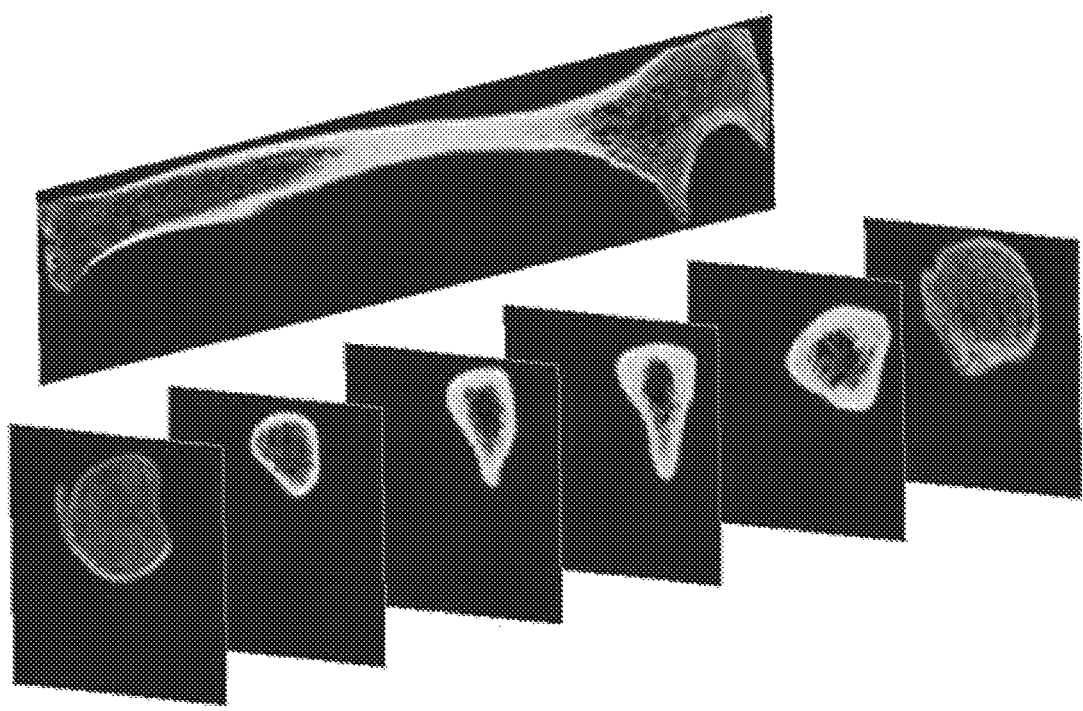

SYSTEMS AND METHODS FOR PATIENT SPECIFIC MODELING OF THE MECHANICAL PROPERTIES OF BONE

CROSS REFERENCE TO RELATED APPLICATION

This application claims the benefit of U.S. Provisional Patent Application Ser. No. 62/512,870 filed May 31, 2017, which is hereby incorporated by reference in its entirety.

FIELD

This application generally relates to patient-specific modeling of the mechanical properties of bone. Specifically, this application relates to systems and methods for patient-specific modeling of bone mechanical integrity with improved determination of the elastic modulus of the patient-specific bone specimens.

BACKGROUND

Bone health affects the overall health and quality of life of people around the world; for example, over 1.5 million older Americans suffer fractures due to weak bones each year. The bony skeleton provides support, allows mobility, protects the body, and serves as a storage area for essential minerals such as calcium, phosphorus and magnesium. Bone is a composite material whose mechanics are dominated by protein and minerals. Collagen protein serves as the framework of the bone and provides toughness and ductility. The minerals, in the form of crystals dispersed around and between collagen fibers, stiffen and strengthen the bone's protein structure.

There are two types of bone: cortical (compact) and cancellous (trabecular or spongy). Cortical bone is configured for support and protection and is arranged as densely packed parallel collagen fibrils organized in layers. This dense cortical bone is located, for example, in the shafts (diaphyses) of the long and short bones of the extremities. Cancellous (trabecular) bone is more a porous type of bone located, for example, at the ends (epiphyses) of long bones and in the vertebrae. Cancellous bone provides necessary stiffness and strength without adding much weight, as it is configured to transfer stresses to the stronger, stiffer, and more dense cortical bone.

Bone is a living tissue that is constantly turning over and regenerating throughout an individual's lifespan. Old bone is broken down (resorbed), creating a void, and new bone is formed in the void. Under normal conditions there is a continuous cyclic remodeling of bone, where osteoclasts remove old and micro damaged bone by acidification and proteolytic digestion, and osteoblasts secrete collagen and other specialized matrix proteins and minerals to synthesize new bone. Many hormones, including vitamin D, parathyroid hormone, calcitonin, estrogen, and testosterone, are involved in the regulation and complex interaction between the skeleton, intestine, and kidneys to maintain mineral homeostasis in the bloodstream. Day-to-day survival and overall bone health largely rely on the proper balance of such hormones. Additionally, adequate nutrition and high impact physical activity are contributors to adequate bone health. During childhood and through the teenage years, normal healthy bones experience more bone formation than resorption. However, as humans age, increased bone resorption, decreased bone formation, or a combination of both, lead to a weakening of bones as the net result is less bone formation than resorption.

Further, bone diseases may disrupt normal bone functioning and can make bones weak. One common bone disease is osteoporosis. Osteoporosis is a skeletal disorder characterized by decreased bone strength predisposing an individual to an increased risk of fracture. There are two types of osteoporosis: (1) Type 1 osteoporosis is characterized by a rapid loss of cancellous bone and a small loss of cortical bone in the hips, spine, and wrists of postmenopausal women; and (2) Type 2 (senile) osteoporosis affects both elderly men and women and, is characterized by a loss of cortical and cancellous bone in predominantly cortical bone sites, which is where a majority of non-vertebral fractures after the age of 60 occur in both men and women.

The strength of bone depends on the quality of the bone including the architecture, turnover, damage accumulation, and mineralization of the bone. Bone mineral density (BMD) describes the amount of mineral per unit area or volume measured and is believed to account for only approximately 70% of bone strength. Current techniques used to diagnose osteoporosis and identify fracture risk focus primarily on measuring bone mineral density. One such technique of measuring BMD is Dual X-ray absorptiometry (DXA). DXA noninvasively measures the transmission of x-rays with high and low energy photons through the body. A DXA measurement represents the sum of cortical and trabecular bone within the bone area scanned as part of the procedure. The results of a DXA scan are presented as a Z score and a T score, where the Z score is the number of standard deviations the measured result is from the mean for age and sex and the T score compares the measured BMD result with the average BMD of healthy 29 year old white women.

Other such techniques used to measure BMD include peripheral quantitative computed tomography (pQCT) and high resolution peripheral quantitative computed tomography (HRpQCT), in which 2-dimensional CT images are made from many different angles around the body or limb and processed by a computer to create a 3-dimensional representation of a body part. These 3-dimensional measurements of bone density and structure can be used as inputs for mechanical analyses including finite element analyses of bone stiffness and strength.

However, such techniques of measuring BMD are limited in that they are not capable of providing direct mechanical measurements of the mechanical properties of a specific patient's bone. For example, changes in the mechanical properties of the bone from lifestyle, diet, or genetic factors can increase fracture risk while leaving bone mineral density intact, thus remaining undetected by such conventional screening methods.

Investigators have sought to improve assessment of the mechanical properties of bone through finite element analysis (FEA) of 3-dimensional computer models of bones. Patient-specific geometry of bone tissue is derived from computed tomography (CT) images, which show the mineral in the bones of a particular patient. However, the elastic modulus (E) of bone tissue that must be used in the FEA calculation is not patient specific. Instead, average values for E determined from previous ex-vivo studies of cadaveric or animal bones must be applied to all patients regardless of accuracy in representing a patient specifically.

Further, current techniques, such as DXA, are deficient in accurately diagnosing a fracture risk in an osteoporotic patient. Specifically, in prospective studies most post-menopausal women diagnosed with osteoporosis do not suffer an osteoporotic fracture and conversely, most osteoporotic fractures occur among woman diagnosed as not having osteoporosis. The rate of false positive and false negative for fracture risk is exceedingly high. Thus, the inventors recognize a need for methods and systems for patient specific modeling of the mechanical properties of bone.

SUMMARY

It is against this background that the present disclosure provides systems and methods for patient specific modeling of the mechanical properties of bone.

In various embodiments, a method of patient-specific modeling of the mechanical properties of bone is disclosed. The method includes (1) obtaining a bending stiffness (K) of a bone specimen non-invasively and non-destructively in a dynamic 3-point bending test; (2) determining a flexural rigidity (EI) of the bone specimen based on the obtained K in accordance with the equation $EI=KL^3/48$ where L represents the length of the bone specimen; (3) imaging the bone specimen to create a geometric model of the bone specimen; (4) creating a mathematical mechanical model in silico of the bone specimen from the geometric model; (5) assigning an elastic modulus (E) to the bone specimen of the mathematical mechanical model; (6) determining the flexural rigidity of the bone specimen from simulating the mathematical mechanical model; (7) determining a discrepancy between the flexural rigidity of the bone specimen from the simulated mechanical model and the flexural rigidity of the bone specimen based on the obtained K; (8) adjusting the elastic modulus of the bone specimen of the simulated mathematical mechanical model to minimize the discrepancy and repeating steps 6-7; (9) repeating step 8 until an optimized elastic modulus is determined where the discrepancy is reduced below or to a predetermined threshold; and (10) applying the optimized elastic modulus to the simulated mathematical mechanical model to determine a strength of the bone, where the optimized elastic modulus represents a patient-specific E of the bone specimen.

In other embodiments, a system for patient-specific modeling of the mechanical properties of bone is disclosed. The system for patient-specific modeling of bone mechanical integrity includes a device for measuring the bending stiffness (K) of a bone specimen in vivo and a data analyzer. The data analyzer includes a storage medium containing computer readable and executable instructions for collecting the bending stiffness of the bone specimen from the device for measuring the bending stiffness of a bone specimen in vivo and imaging of the bone specimen from an imaging device and a processor. The processor is for executing instructions to determine a flexural rigidity (EI) of the bone specimen based on the obtained K in accordance with the equation $EI=KL^3/48$ where L represents the length of the bone specimen, create a mathematical mechanical model of the bone specimen from the geometric model, assign an elastic modulus (E) to the bone specimen of the mathematical mechanical model, determine the flexural rigidity of the bone specimen from simulating the mathematical mechanical model, determine a discrepancy between the flexural rigidity of the bone specimen from the simulated mechanical model and the flexural rigidity of the bone specimen based on the obtained K, adjust the elastic modulus of the bone specimen of the simulated mathematical mechanical model to minimize the discrepancy until an optimized elastic modulus is determined where the discrepancy is reduced below or to a predetermined threshold, and apply the optimized elastic modulus to the simulated mathematical mechanical model to determine a strength of the bone, where the optimized elastic modulus represents a patient-specific E of the bone specimen.

BRIEF DESCRIPTION OF THE DRAWINGS

A more complete appreciation of the disclosure and the many embodiments thereof will be better understood by reference to the following detailed description when considered in connection with the accompanying drawings, wherein:

FIG. 1 depicts a CT scan of a representative ulna

The provided drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several embodiments of the invention, and together with the description serve to explain the principles of the invention; it being understood, however, that the invention is not limited to the precise arrangements shown.

DETAILED DESCRIPTION OF THE INVENTION

Specific embodiments of the present application will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art. The terminology used in the description herein is for describing particular embodiments only and is not intended to be limiting. As used in the specification and appended claims, the singular forms "a," "an," and "the" are intended to include the plural forms as well, unless the context clearly indicates otherwise.

Recitations of "at least one" component, element, etc. in the present disclosure and appended claims should not be used to create an inference that the alternative use of the articles "a" or "an" should be limited to a single component, element, etc.

In the present disclosure and appended claims, recitations of a component being "configured" to embody a particular property, or function in a particular manner, are structural recitations, as opposed to recitations of intended use. More specifically, references to the manner in which a component is "configured" denotes an existing physical condition of the component and, as such, is to be taken as a definite recitation of the structural characteristics of the component.

As used in the present disclosure and appended claims, terms like "preferably," "commonly," and "typically" are not utilized to limit the scope of the claims or to imply that certain features are critical, essential, or even important to the structure or function of the claimed embodiments. Rather, these terms are merely intended to identify particular aspects of an embodiment of the present disclosure or to emphasize alternative or additional features that may or may not be utilized in a particular embodiment of the present disclosure.

The terms "substantially" and "approximately," as used in the present disclosure and appended claims, represent the inherent degree of uncertainty that may be attributed to any quantitative comparison, value, measurement, or other representation. Such terms are also utilized to represent the degree by which a quantitative representation may vary from a stated reference without resulting in a change in the basic function of the subject matter at issue.

Unless otherwise indicated, all numbers expressing quantities, properties, conditions, and so forth as used in the specification and claims are to be understood as being modified in all instances by the term "about." Additionally, the disclosure of any ranges in the specification and claims are to be understood as including the range itself and also anything subsumed therein, as well as endpoints. Notwithstanding that numerical ranges and parameters setting forth the broad scope of the disclosure are approximations, the numerical values set forth in the specific examples are reported as precisely as possible. Any numerical values, however, inherently contain certain errors necessarily resulting from error found in their respective measurements.

"Automatically" includes the use of a machine to conduct a particular action. The process by which data is extracted, organized and stored is a data-driven and largely automatic process and may utilize a computer network (e.g., wide area network, such as the internet, a local area network, a mobile communications network, a public service telephone network, and/or any other network) and may be configured to electronically connect a user computing device (e.g., a PC) and a server computing device (e.g., cloud, mainframe, or other server device).

"Calculate" includes automatically determining or ascertaining a result.

"Computer" includes a machine (e.g., desktop, laptop, tablet, smartphone, television, server, as well as other current or future computer instantiations) containing a computer processor that has been specially configured with a set of computer executable instructions. References to "at least one" computer are intended to encompass both autonomous systems and sub-systems as well as situations where a given functionality might be divided across multiple machines (e.g. parallel processing) for efficiency or other purposes.

"Data Receiver" as used herein includes any component configured to receive data.

"Exemplary" as used herein means giving an example; serving as an illustration or example of something.

"GUI" or "Graphical User Interface" includes a user interface displayed on a visual subsystem (e.g., desktop monitor, tablet/phone screen, interactive television screen, etc.) by which users interact with electronic devices via images (e.g., lists, hyperlinks, panels, etc.).

"Patients" as used herein includes any living organism with a calcified skeletal system such as primates, including humans, equines, canines, and felines.

A "Processor" may include any processing component configured to receive and execute instructions (such as from the data storage component and/or memory component). Network interface hardware may include any wired/wireless hardware generally known to those of skill in the art for communicating with other networks and/or devices.

A "Server" may be specially configured or configured as a general purpose computer with the requisite hardware, software, and/or firmware. A server may include a processor, input/output hardware, network interface hardware, a data storage component (which stores data and/or metadata) and a memory component configured as volatile or non-volatile memory including RAM (e.g., SRAM, DRAM, and/or other types of random access memory), flash memory, registers, compact discs (CDs), digital versatile discs (DVD), and/or other types of storage components. A memory component may also include operating logic that, when executed, facilitates the operations described herein. An administrative computing device may also be employed to facilitate manual corrections to the metadata.

In embodiments, a method for determining patient-specific modeling of the mechanical properties of bone is disclosed. The method combines bone properties ascertained from dynamic 3-point bending testing with a geometric bone model developed from non-invasive imaging techniques to create an optimized mathematical mechanical model of the patient-specific bone specimen.

In embodiments, a bending stiffness (K) of a bone specimen is obtained non-invasively and non-destructively in a dynamic 3-point bending test. Non-invasive, as used herein, is a procedure that does not require incision or puncture of the skin. Similarly, non-destructive, as used herein, is a procedure that does not result in damage including breakage or fracture of the bone specimen. The bending stiffness of the bone specimen is desirably obtained non-invasively and non-destructively as measurements are preferably obtained in-vivo on living patients. Utilization of non-invasive and non-destructive measurements eliminates the need for healing and recovery of the patient after measurement.

In embodiments, the bone specimen is a long bone, such as, e.g., the ulna or the humerus in the human arm or the tibia or femur in the human leg. In further embodiments, the bone specimen may be a bone from a non-human animal. In yet further embodiments, the bone specimen may be a non-long bone such as the pelvis, rib, spine, jaw, or skull.

In one or more embodiments, the bending stiffness is obtained using Mechanical Response Tissue Analysis (MRTA). MRTA has been developed for the noninvasive determination of mechanical properties of the constituents of an intact limb of a patient. MRTA utilizes a vibratory unit which is placed against the bone and overlying soft tissue of the bone specimen to be monitored. The vibratory unit provides accurate response measurements for a range of frequencies which provide information of the soft tissue and the underlying bone. The vibratory unit contains transducers which output tissue-response signals related to force and acceleration in the range of frequencies which are broken down to yield accelerance (i.e. acceleration/force) data, typically including real and imaginary accelerance frequency response data. The physical parameters of the patient's tested limb are determined by correlating compliance (i.e. displacement/force) and stiffness (force/displacement) data derived from the accelerance data with the behavior of a linear mechanical system having coupled bone and skin masses, springs and dampers and whose equations of motion contain the physical parameters to be determined. Details of an example MRTA system are provided in U.S. Pat. No. 5,006,984 issued Apr. 9, 1991 and entitled BONE/TISSUE ANALYZER AND METHOD, the contents of which are incorporated herein in their entirety.

Additionally, further details of an example MRTA system are provided in International Application No. PCT/US2014/033816, filed Apr. 11, 2014 which claims priority to U.S. Provisional Patent Application No. 61/811,037, filed Apr. 11, 2013, the details of both of which are incorporated herein in their entirety. PCT/US2014/033816 provides in part that the first step of MRTA generally involves the collection of data in the form of a complex accelerance frequency response function, A(f). The second step of MRTA generally involves calculation of associated complex compliance and stiffness frequency response functions, Y(f) and H(f), respectively. The third step of MRTA generally involves the analysis of these complex compliance and stiffness frequency response functions, Y(f) and H(f), by fitting Y(f) and H(f) to a parametric mathematical model of the skin-bone complex to estimate the values of mechanical properties thereof. The parametric mathematical model takes the form of a complex rational polynomial.

In embodiments, a flexural rigidity (EI) of the bone specimen is determined based on the bending stiffness obtained from the non-invasive and non-destructive dynamic 3-point bending test such as MRTA. With a known or approximated bending stiffness of the bone specimen and known or approximated length of the bone specimen the flexural rigidity may be calculated. For a simply supported beam of length L, the bending stiffness is calculated according to equation 1 provided infra.

$$EI = KL^3/48 \tag{1}$$

In embodiments, the patient's bone specimen is imaged to create a geometric model of the bone specimen. In various embodiments, the bone specimen is imaged with one or more imaging modalities, such as, computed tomography (CT) imaging, dual-energy X-ray absorptiometry (DXA), and magnetic resonance imaging (MRI). The imaging techniques allow development of models of patient-specific geometry of bones tissue. For example, CT images show the mineralized tissues in the bones of a particular patient clearly and allow for the extraction of a 3D model of the bone specimen structure based on the indication of bone opposed to soft tissue in the images. With reference to FIG. 1, a CT scan of a representative ulna is provided with a lateral view showing a longitudinal cross-section of the entire bone and a series of six transverse views showing the geometry and bone density changes along the length of the shaft of the ulna. The brightness value of a pixel in a CT image, traditionally expressed in Hounsfield units (HU), reflects the spatially averaged bone mineral density within that pixel. Without wishing to be bound by theory, it is believed that a summation or integration of the brightness values distributed over an entire bone volume correlates with bone stiffness and strength as the brightness values are representative of the bone mineral density of the bone. The summation or integration of the brightness values may include a weighting of each pixel brightness. However, the magnitude of the stiffness and strength remains unknown as the brightness value of each pixel only provides bone mineral density relative to other locations within the CT image and mineral density does not perfectly correlate to stiffness or strength of the bone.

In embodiments, a simulated mechanical model of the bone specimen is created based on the framework of the geometric model. The geometric model of the bone specimen provides the spatial envelope of the bone specimen as well as information related to density, porosity, and other physical properties of the bone structure. Using the geometric model and baseline or estimated mechanical properties for the bone specimen, a simulated mechanical model of the bone specimen may be generated.

In one or more embodiments, the mathematical mechanical model is constructed as a direct model approximating Euler beam theory or Timoshenko beam theory. To develop the mathematical mechanical model for the bone specimen, a CT image is collected of the bone specimen. The collected CT image is a collection of slices which are radiographic cross sections of the bone specimen, such as an arm. Each cross section may be evaluated, as follows: each pixel of the CT image representing bone is identified by its brightness and connectivity to the rest of the bone specimen, its location and HU is counted to infer a flexural rigidity (EI) value for that cross section. The correlation between HU and E for each pixel is tuned or optimized as part of this process. The EI for each cross section is combined into a mathematical model of the long bone represented as a beam with a non-constant cross section. Euler beam theory is modeled in accordance with Equation 2 where w is the deflection, x is the coordinate direction of the long axis of the bone, and f is the known loading function.

$$\frac{d^2}{dx^2}\left(EI\frac{d^2w}{dx^2}\right) = f \tag{2}$$

From this, the displacement, angular displacement, moment and shear load can be calculated by integration. From the known moment and knowledge of the distribution of bone in each cross section, the greatest stress can be deduced.

Timoshenko beam theory is an extension to Euler beam theory in that shear deformation is added into the differential equation for deflection. Timoshenko beam theory may add accuracy as bones get squatter, or if the anisotropy of the bone becomes significant. Timoshenko beam theory is modeled in accordance with two coupled differential equations, Equations 3 and 4 where w is the deflection, x is the coordinate direction of the long axis of the bone, f is the known loading function, Ψ is the rotation of the cross section about the axis of bending, GA is the shear modulus multiplied by the cross sectional area, and K is a shear correction factor that changes with cross sectional geometry.

$$\frac{d}{dx}\left[\kappa GA\left(\Psi + \frac{dw}{dx}\right)\right] = f \tag{3}$$

$$\frac{d}{dx}\left(EI\frac{d\Psi}{dx}\right) - \kappa GA\left(\Psi + \frac{dw}{dx}\right) = 0 \tag{4}$$

In one or more embodiments, the mechanical model is constructed as a 1-dimensional finite element analysis (FEA) model based on Euler beam theory or Timoshenko beam theory. There are multiple numerical and analytic methods to solve for beam bending based upon Euler and Timoshenko beam theory. One method suited to the piecewise nature of the bone properties seen on CT images is 1-dimensional finite element analysis. In 1-dimensional FEA the distance of longitudinal bone represented by each slice obtained from the CT images, typically 0.5 to 1 mm, is treated a single beam element in a larger beam model of the arm. This 1-dimensional FEA analysis converts the fourth order differential equation representing either Euler beam theory (Equation 2) or Timoshenko beam theory (Equations 3 and 4), into a matrix of simultaneous algebraic equations which can be solved digitally.

In one or more embodiments, the mechanical model is constructed as a 3-dimensional finite element analysis (FEA) model based on the theory of elasticity. For 3-dimensional FEA, the full 3D geometry of the bone is deduced from the CT scans by a process called segmentation. In segmentation, the geometry of the bone is broken into a large number of regular 3D elements in a process called meshing. Typically $10^3$ to $10^5$ 3D elements are generated during the meshing process. Boundary conditions representing the supports during mechanical testing, as well as the applied load, are added to the mechanical model. Finally, material properties are assigned to the bone, either in a homogenous nature, where all bone is given the same value of stiffness, or distributed in a nonhomogenous nature, using the mineral content distribution within the bone as revealed by HU of each pixel. The model is then simulated using elasticity theory by converting continuous differential equations into thousands of simultaneous linear equations.

In embodiments, an elastic modulus (E), alternatively known as Young's modulus, is assigned to the bone specimen of the mechanical model. In embodiments, the elastic modulus for utilization in the simulated mechanical model is assigned assuming the bone specimen has a uniform value for the elastic modulus throughout the bone specimen such that the elastic modulus is homogenous. In further embodiments, the elastic modulus for utilization in the simulated mechanical model is assigned assuming the bone specimen has a non-uniform or heterogeneous value for the elastic modulus.

When assuming the bone specimen has a uniform or homogenous elastic modulus throughout the bone specimen, the initial assigned value for the elastic modulus may be obtained, for example, from averaged or median values of the elastic modulus from previously obtained values from cadaveric or animal bones in research studies. It will be appreciated that the initial assigned value for the elastic modulus may also be obtained, for example, from a look-up table or database based on the species of patient, the mass of the patient, the height or length of the patient, or other physiological attributes of the patient.

When assuming the bone specimen has a non-uniform or heterogeneous elastic modulus throughout the bone specimen, the value for the elastic modulus may be determined based upon the brightness of each pixel in the imaging of the bone specimen by a CT machine for example. Since the brightness of each pixel of the imaging is related to the mineralization of the bone specimen at the corresponding location it may be posited that the elastic modulus will vary in relation to the pixel brightness. In various embodiments, the relationship between the pixel brightness and the relative elastic modulus may be based on a linear relationship, a power law relationship, or other algebraic relationships or algorithms.

In embodiments where the relative values of the elastic modulus are generated based on a linear relationship with the relative brightness values of the individual pixels of the imaging of the bone specimen, the brightest and dimmest pixels may be assigned anchor elastic modulus values with a linear scale correlating the pixel brightness and the elastic modulus between the anchor elastic modulus values. Alternatively, a baseline elastic modulus may be chosen and assigned to the average or median pixel brightness with brighter and dimmer pixels being assigned increased or decreased elastic modulus values with a linear relationship to the deviation from the average or median pixel brightness. The anchor elastic modulus and baseline elastic modulus values may be obtained, for example, from averaged or median values of the elastic modulus from previously obtained values from cadaveric or animal bones in research studies or from a look-up table or database based on the species of patient, the mass of the patient, the height or length of the patient, or other physiological attributes of the patient.

In embodiments where the relative values of the elastic modulus are generated based on a power law relationship with the relative brightness values of the individual pixels of the imaging of the bone specimen, the brightest and dimmest pixels may be assigned anchor elastic modulus values with a power law relationship correlating the pixel brightness and the elastic modulus between the anchor elastic modulus values. Alternatively, a baseline elastic modulus may be chosen and assigned to the average or median pixel brightness with brighter and dimmer pixels being assigned increased or decreased elastic modulus values with a power law relationship to the deviation from the average or median pixel brightness. The anchor elastic modulus and baseline elastic modulus values may be obtained, for example, from averaged or median values of the elastic modulus from previously obtained values from cadaveric or animal bones in research studies or from a look-up table or database based on the species of patient, the mass of the patient, the height or length of the patient, or other physiological attributes of the patient.

In embodiments, the simulated mechanical model generates a bending stiffness (K) of the bone specimen modeled by the mechanical model. From the K value obtained from the simulated mechanical model the flexural rigidity (EI) may be generated in accordance with equation 1, previously presented.

In embodiments, a discrepancy between the flexural rigidity of the bone specimen from the simulated mechanical model and the flexural rigidity of the bone specimen based on the obtained K from the dynamic 3-point bending testing, such as MRTA, is determined. The elastic modulus of the simulated mechanical model is then adjusted either directly or iteratively to minimize the discrepancy. The elastic modulus of the simulated mechanical model is adjusted and the discrepancy is determined until the discrepancy is reduced to below or equal to a predetermined threshold. In various embodiments, the predetermined threshold for the discrepancy is 0 $Nm^2$, 0.01 $Nm^2$, 0.05 $Nm^2$, 0.1 $Nm^2$, 0.5 $Nm^2$, or 1 $Nm^2$. Once the discrepancy is equal to or drops below the predetermined threshold the elastic modulus applied in the simulated mechanical model is considered the optimized elastic modulus and represents a patient-specific elastic modulus of the bone specimen. It will be appreciated that in embodiments where the bone specimen is considered to have a non-uniform or heterogeneous elastic modulus throughout the bone specimen the optimized elastic modulus will include a relationship between image brightness of the bone specimen images and the elastic modulus.

In embodiments, having determined the optimized elastic modulus which represents a patient-specific elastic modulus for the bone specimen, the optimized elastic modulus may be utilized in the simulated mechanical model or additional mechanical models for patient-specific mechanical analysis of the bone specimen. In various embodiments these mechanical models may include 3-dimensional FEA for example, to provide patient-specific estimations of strength of the bone specimen in bending as well as other loading modes such as compression or at different locations on the bone specimen or in different direction from the initial dynamic 3-point bending test. The patient-specific optimized elastic modulus allows a generated mechanical model to render estimations of strength of the bone specimen throughout the bone specimen and under various loading conditions.

MRTA, and other dynamic 3-point bending tests, additionally provide a patient-specific mass (M) and a patient-specific damping coefficient (B) for the patient's bone specimen. Implementation of the patient-specific mass, patient-specific damping coefficient, other patient-specific information extracted from the MRTA, or combinations thereof into mechanical models also allows for development of mechanical models which include inertial and inelastic (including viscoelastic) effects in dynamic and failure models. Development of models with implementation of M, B, and other patient-specific parameters also allows for patient-specific estimates of yield strength, yield strain, toughness, failure strain, and combinations thereof in nonlinear analysis of failure.

Movement as a human is a dynamic process. In passage through a daily routine a person's bones experience a combination of both static and dynamic loading. An automobile accident, a fall down the stairs, and even walking place different stresses and strains on the skeletal bones than standing or sitting in a static manner. Implementation of a dynamic mechanical model which is patient-specific allows a doctor of a potentially osteoporotic patient, for example, to model the stresses and strains on the bone specimen of the patient throughout their daily routine or even in catastrophic events using patient-specific parameters.

With some loss of intra-patient specificity, the same optimized elastic modulus and other patient-specific parameters may be applied to mechanical simulations of the mechanical properties of bone other than the original bone specimen. Imaging of other bones throughout the patient may be utilized to create geometric models and ultimately mechanical models which utilize the determined optimized elastic modulus. This allows for the patient-specific physiological traits determined from the patient's diet, exercise routine, genetic factors, and other parameters which effect bone health and strength to be accounted for in modeling of other bones than the bone specimen as a result of implementation of the optimized elastic modulus obtained from the bone specimen.

In further embodiments, a system for patient-specific modeling of the mechanical properties of bone is provided. The system includes a device for measuring the bending stiffness of the bone specimen in vivo as well as a data analyzer.

In various embodiments, the device for measuring the bending stiffness of the bone specimen in vivo is an MRTA system as previously disclosed.

In various embodiments of a system for patient-specific modeling of the mechanical properties of bone, the data analyzer includes a storage medium and a processor. The storage medium contains computer readable and executable instructions for collecting the bending stiffness of the bone specimen from the device for measuring the bending stiffness of a bone specimen in vivo and imaging of the bone specimen from an imaging device. The processor is provided for executing the instructions to determine a flexural rigidity (EI) of the bone specimen based on the obtained K in accordance with the equation (1) where L represents the length of the bone specimen, create a mathematical mechanical model of the bone specimen from the geometric model, assign an elastic modulus (E) to the bone specimen of the mathematical mechanical model, determine the flexural rigidity of the bone specimen from simulating the mechanical model, determine a discrepancy between the flexural rigidity of the bone specimen from the simulated mechanical model and the flexural rigidity of the bone specimen based on the obtained K, adjust the elastic modulus of the bone specimen of the simulated mechanical model to minimize the discrepancy until an optimized elastic modulus is determined where the discrepancy is reduced below or to a predetermined threshold, and apply the optimized elastic modulus, where the optimized elastic modulus represents a patient-specific E of the bone specimen, to the simulated mechanical model to determine a strength of the bone.

In further embodiments of a system for patient-specific modeling of the mechanical properties of bone, the processor is connected to a visual subsystem with a graphical user interface (GUI). The visual subsystem and graphical user interface provides information to the technician and/or operator of the system. In various embodiments, the information provided to the technician and/or operator includes displays of the geometric model, simulated mechanic model of the bone specimen, or representation of the elastic modulus of each pixel of the imaging. For example, graphical display of the bone specimen with the elastic modulus for each pixel displayed through color variation or as numerical values at selected positions.

It should now be understood that various aspects of the disclosed invention are described herein and that such aspects may be utilized in conjunction with various other aspects.

In a first aspect, the disclosure provides a method of patient-specific modeling of the mechanical properties of bone. The method includes (1) obtaining a bending stiffness (K) of a bone specimen non-invasively and non-destructively in a dynamic 3-point bending test; (2) determining a flexural rigidity (EI) of the bone specimen based on the obtained K in accordance with the equation $EI=KL^3/48$ where L represents the length of the bone specimen; (3) imaging the bone specimen to create a geometric model of the bone specimen; (4) creating a mathematical mechanical model of the bone specimen from the geometric model; (5) assigning an elastic modulus (E) to the bone specimen of the mathematical mechanical model; (6) determining the flexural rigidity of the bone specimen from simulating the mechanical model; (7) determining a discrepancy between the flexural rigidity of the bone specimen from the simulated mechanical model and the flexural rigidity of the bone specimen based on the obtained K; (8) adjusting the elastic modulus of the bone specimen of the simulated mechanical model to minimize the discrepancy and repeating steps 6-7; (9) repeating step 8 until an optimized elastic modulus is determined where the discrepancy is reduced below or to a predetermined threshold; and (10) applying the optimized elastic modulus to the simulated mechanical model to determine a strength of the bone, where the optimized elastic modulus represents a patient-specific E of the bone specimen.

In a second aspect, the disclosure provides a method of the first aspect, in which the bone specimen is in-vivo.

In a third aspect, the disclosure provides a method of any of the first or the second aspect, in which the bending stiffness is obtained from mechanical response tissue analysis (MRTA).

In a fourth aspect, the disclosure provides a method of any of the first to the third aspects, in which the bone specimen is imaged with at least one of computed tomography (CT), dual-energy X-ray absorptiometry (DXA), and magnetic resonance imaging (MRI).

In a fifth aspect, the disclosure provides a method of any of the first to the fourth aspects, in which the bone specimen is imaged with CT imaging.

In a sixth aspect, the disclosure provides a method of any of the first to the fifth aspects, in which the simulated mechanical model of the bone specimen is constructed as a direct mechanical model based on Euler beam theory or Timoshenko beam theory.

In a seventh aspect, the disclosure provides a method of any of the first to the fifth aspects, in which the simulated mechanical model of the bone specimen is constructed as a 1-dimensional finite element analysis (FEA) model based on Euler beam theory or Timoshenko beam theory.

In a eighth aspect, the disclosure provides a method of any of the first to the fifth aspects, in which the simulated mechanical model of the bone specimen is constructed as a 3-dimensional FEA model based on the theory of elasticity.

In a ninth aspect, the disclosure provides a method of any of the first to eighth aspects, in which the elastic modulus is heterogeneous throughout the bone samples with the relative brightness values of individual pixels in the imaging of the bone specimen providing relative values of the elastic modulus at each location of the bone specimen.

In a tenth aspect, the disclosure provides a method of any of the first to ninth aspects, in which the relative values of the elastic modulus are generated based on a linear relationship with the relative brightness values of the individual pixels of the imaging of the bone specimen.

In a eleventh aspect, the disclosure provides a method of any of the first to ninth aspects, in which the relative values of the elastic modulus are generated based on a power law relationship with the relative brightness values of the individual pixels of the imaging of the bone specimen.

In a twelfth aspect, the disclosure provides a method of any of the first to ninth aspects, in which the relative values of the elastic modulus are generated based on an algebraic relationship with the relative brightness values of the individual pixels of the imaging of the bone specimen.

In a thirteenth aspect, the disclosure provides a method of any of the first to the twelfth aspects, in which the elastic modulus is homogenous throughout the bone sample.

In a fourteenth aspect, the disclosure provides a method of any of the first to the twelfth aspects, in which the bone specimen is a human ulna bone.

In a fifteenth aspect, the disclosure provides a system for patient-specific modeling of the mechanical properties of bone. The system includes a device for measuring the bending stiffness (K) of a bone specimen in vivo and a data analyzer. The data analyzer includes a storage medium containing computer readable and executable instructions for collecting the bending stiffness of the bone specimen from the device for measuring the bending stiffness of a bone specimen in vivo and imaging of the bone specimen from an imaging device; and a processor for executing instructions to determine a flexural rigidity (EI) of the bone specimen based on the obtained K in accordance with the equation $EI=KL^3/48$ where L represents the length of the bone specimen, create a mathematical mechanical model of the bone specimen from the geometric model, assign an elastic modulus (E) to the bone specimen of the mathematical mechanical model, determine the flexural rigidity of the bone specimen from simulating the mathematical mechanical model, determine a discrepancy between the flexural rigidity of the bone specimen from the simulated mechanical model and the flexural rigidity of the bone specimen based on the obtained K, adjust the elastic modulus of the bone specimen of the simulated mechanical model to minimize the discrepancy until an optimized elastic modulus is determined where the discrepancy is reduced below or to a predetermined threshold, and apply the optimized elastic modulus to the simulated mechanical model to determine a strength of the bone, where the optimized elastic modulus represents a patient-specific E of the bone specimen.

Having shown and described various embodiments in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

As will be evident from the foregoing disclosure, the methods of the invention are carried out non-invasively.

The invention claimed is:

1. A method of patient-specific modeling of the mechanical properties of bone comprising:
   (1) obtaining a bending stiffness (K) of a bone specimen non-invasively and non-destructively in a dynamic 3-point bending test;
   (2) determining a flexural rigidity (EI) of the bone specimen based on the obtained K in accordance with the equation $EI=KL^3/48$ where L represents the length of the bone specimen;
   (3) imaging the bone specimen to create a geometric model of the bone specimen;
   (4) creating a mathematical mechanical model of the bone specimen from the geometric model;
   (5) assigning an elastic modulus (E) to the bone specimen of the mathematical mechanical model;
   (6) determining the flexural rigidity of the bone specimen from simulating the mathematical mechanical model;
   (7) determining a discrepancy between the flexural rigidity of the bone specimen from the simulated mechanical model and the flexural rigidity of the bone specimen based on the obtained K;
   (8) adjusting the elastic modulus of the bone specimen of the simulated mechanical model to minimize the discrepancy and repeating steps 6-7;
   (9) repeating step 8 until an optimized elastic modulus is determined where the discrepancy is reduced below or to a predetermined threshold; and
   (10) applying the optimized elastic modulus to the simulated mechanical model to determine a strength of the bone, where the optimized elastic modulus represents a patient-specific E of the bone specimen.

2. The method of patient-specific modeling of the mechanical properties of bone of claim 1, where the bone specimen is in-vivo.

3. The method of patient-specific modeling of the mechanical properties of bone of claim 1, where the bending stiffness is obtained from mechanical response tissue analysis (MRTA).

4. The method of patient-specific modeling of the mechanical properties of bone of claim 1, where the bone specimen is imaged with at least one of computed tomography (CT), dual-energy X-ray absorptiometry (DXA), and magnetic resonance imaging (MRI).

5. The method of patient-specific modeling of the mechanical properties of bone of claim 4, where the bone specimen is imaged with CT imaging.

6. The method of patient-specific modeling of the mechanical properties of bone of claim 1, where the simulated mechanical model of the bone specimen is constructed as a direct mechanical model based on Euler beam theory or Timoshenko beam theory.

7. The method of patient-specific modeling of the mechanical properties of bone of claim 1, where the simulated mechanical model of the bone specimen is constructed as a 1-dimensional finite element analysis (FEA) model based on Euler beam theory or Timoshenko beam theory.

8. The method of patient-specific modeling of the mechanical properties of bone of claim 1, where the simulated mechanical model of the bone specimen is constructed as a 3-dimensional FEA model based on the theory of elasticity.

9. The method of patient-specific modeling of the mechanical properties of bone of claim 1, where the elastic modulus is heterogeneous throughout the bone samples with the relative brightness values of individual pixels in the imaging of the bone specimen providing relative values of the elastic modulus at each location of the bone specimen.

10. The method of patient-specific modeling of the mechanical properties of bone of claim 9, where the relative values of the elastic modulus are generated based on a linear relationship with the relative brightness values of the individual pixels of the imaging of the bone specimen.

11. The method of patient-specific modeling of the mechanical properties of bone of claim 9, where the relative values of the elastic modulus are generated based on a power law relationship with the relative brightness values of the individual pixels of the imaging of the bone specimen.

12. The method of patient-specific modeling of the mechanical properties of bone of claim 9, where the relative values of the elastic modulus are generated based on an algebraic relationship with the relative brightness values of the individual pixels of the imaging of the bone specimen.

13. The method of patient-specific modeling of the mechanical properties of bone of claim 1, where the elastic modulus is homogenous throughout the bone sample.

14. The method of patient-specific modeling of the mechanical properties of bone of claim 1, where the bone specimen is a human ulna bone.

15. A system for patient-specific modeling of the mechanical properties of bone, the system comprising a device for measuring the bending stiffness (K) of a bone specimen in vivo and a data analyzer:

the data analyzer comprising:
a storage medium containing computer readable and executable instructions for collecting the bending stiffness of the bone specimen from the device for measuring the bending stiffness of a bone specimen in vivo and imaging of the bone specimen from an imaging device; and
a processor for executing instructions to:
determine a flexural rigidity (EI) of the bone specimen based on the obtained K in accordance with the equation $EI=KL^3/48$ where L represents the length of the bone specimen,
create a mathematical mechanical model of the bone specimen from the geometric model, assign an elastic modulus (E) to the bone specimen of the mathematical mechanical model,
determine the flexural rigidity of the bone specimen from simulating the mathematical mechanical model,
determine a discrepancy between the flexural rigidity of the bone specimen from the simulated mechanical model and the flexural rigidity of the bone specimen based on the obtained K,
adjust the elastic modulus of the bone specimen of the simulated mechanical model to minimize the discrepancy until an optimized elastic modulus is determined where the discrepancy is reduced below or to a predetermined threshold, and
apply the optimized elastic modulus to the simulated mechanical model to determine a strength of the bone, where the optimized elastic modulus represents a patient-specific E of the bone specimen.

* * * * *